(12) United States Patent
Kezirian et al.

(10) Patent No.: US 8,764,632 B2
(45) Date of Patent: Jul. 1, 2014

(54) ENDOSCOPIC DEVICE AND SYSTEM

(75) Inventors: Eric James Kezirian, San Francisco, CA (US); Robert Andrew Howard, Palo Alto, CA (US); Jonathan Patrick Summers, Pacifica, CA (US); Jeffrey William Servaites, San Francisco, CA (US); Matthew Charles Archer Durack, San Francisco, CA (US)

(73) Assignee: Eric James Kezirian, San Francisco, CA (US)

( * ) Notice: Subject to any disclaimer, the term of this patent is extended or adjusted under 35 U.S.C. 154(b) by 297 days.

(21) Appl. No.: 13/071,937

(22) Filed: Mar. 25, 2011

(65) Prior Publication Data
US 2011/0251457 A1    Oct. 13, 2011

Related U.S. Application Data

(60) Provisional application No. 61/321,911, filed on Apr. 8, 2010.

(51) Int. Cl.
*A61B 1/04* (2006.01)
*A61B 1/00* (2006.01)

(52) U.S. Cl.
USPC .......................... 600/109; 600/101; 600/113

(58) Field of Classification Search
CPC .... A61B 1/00181; A61B 1/05; A61B 1/0125; A61B 1/00174; A61B 17/24
USPC ......... 600/109, 104, 435, 101, 114, 182, 165, 600/112, 113, 103, 111, 166, 160; 606/196, 606/16, 27, 108; 348/65, 45
See application file for complete search history.

(56) References Cited

U.S. PATENT DOCUMENTS

| | | | |
|---|---|---|---|
| 1,538,191 A | 5/1925 | Lando | |
| 4,265,561 A | 5/1981 | Heckele | |
| 4,784,117 A | 11/1988 | Miyazaki | |
| 4,797,736 A | 1/1989 | Kloots et al. | |
| 5,039,198 A | 8/1991 | VanBeek | |
| 5,166,787 A * | 11/1992 | Irion ............................... | 348/75 |
| 5,178,130 A * | 1/1993 | Kaiya ........................... | 600/109 |
| 5,305,098 A * | 4/1994 | Matsunaka et al. ............. | 348/65 |
| 5,341,240 A | 8/1994 | Broome | |
| 5,368,015 A * | 11/1994 | Wilk .............................. | 600/104 |
| 5,381,784 A * | 1/1995 | Adair ............................. | 600/166 |
| 5,519,532 A | 5/1996 | Broome | |
| 5,604,531 A | 2/1997 | Iddan et al. | |
| 5,653,677 A * | 8/1997 | Okada et al. ................... | 600/112 |

(Continued)

FOREIGN PATENT DOCUMENTS

| | | |
|---|---|---|
| CN | 2609498 | 4/2004 |
| CN | 2620530 | 6/2004 |

(Continued)

*Primary Examiner* — John P Leubecker
*Assistant Examiner* — Ronald D Colque
(74) *Attorney, Agent, or Firm* — Brooks Kushman P.C.

(57) ABSTRACT

An endoscopic system may include a catheter or tubing and at least one optical sensor disposed along the catheter or tubing and configured to capture image information from a body lumen when disposed within the body lumen and activated. The system may further include an untethered module operatively arranged with the at least one optical sensor and configured to store or transmit image information captured by the at least one optical sensor. The catheter or tubing, at least one optical sensor and module may be portable during use.

11 Claims, 5 Drawing Sheets

(56) References Cited

U.S. PATENT DOCUMENTS

| | | | |
|---|---|---|---|
| 5,746,693 A | 5/1998 | Spitz et al. | |
| 5,940,126 A | 8/1999 | Kimura | |
| 5,976,071 A | 11/1999 | Sekiya | |
| 6,066,090 A * | 5/2000 | Yoon | 600/113 |
| 6,106,456 A | 8/2000 | Storz | |
| 6,139,490 A | 10/2000 | Breidenthal et al. | |
| 6,186,944 B1 | 2/2001 | Tsai | |
| 6,361,489 B1 | 3/2002 | Tsai | |
| 6,561,972 B2 | 5/2003 | Ooshima et al. | |
| 6,626,825 B2 | 9/2003 | Tsai | |
| 6,632,172 B1 | 10/2003 | Igarashi | |
| 6,833,952 B2 | 12/2004 | Yamamoto | |
| 6,855,110 B2 | 2/2005 | Igarashi | |
| 6,875,169 B2 | 4/2005 | Berci et al. | |
| 6,934,575 B2 | 8/2005 | Ferre et al. | |
| 6,960,161 B2 | 11/2005 | Amling et al. | |
| 6,986,738 B2 * | 1/2006 | Glukhovsky et al. | 600/109 |
| 7,029,435 B2 * | 4/2006 | Nakao | 600/153 |
| 7,087,013 B2 | 8/2006 | Belson et al. | |
| 7,108,657 B2 | 9/2006 | Irion et al. | |
| 7,116,352 B2 | 10/2006 | Yaron | |
| 7,137,948 B2 | 11/2006 | Tsai | |
| 7,267,647 B2 | 9/2007 | Okada et al. | |
| 7,316,646 B2 | 1/2008 | Amling et al. | |
| 7,318,802 B2 | 1/2008 | Suzuki et al. | |
| 7,322,934 B2 * | 1/2008 | Miyake et al. | 600/173 |
| 7,419,467 B2 | 9/2008 | Tsai | |
| 7,448,993 B2 * | 11/2008 | Yokoi et al. | 600/114 |
| 7,621,869 B2 * | 11/2009 | Ratnakar | 600/173 |
| 7,662,089 B2 * | 2/2010 | Okada et al. | 600/113 |
| 8,182,415 B2 * | 5/2012 | Larkin et al. | 600/104 |
| 8,197,399 B2 * | 6/2012 | Bayer et al. | 600/113 |
| 8,277,373 B2 * | 10/2012 | Maahs et al. | 600/107 |
| 8,289,381 B2 * | 10/2012 | Bayer et al. | 348/65 |
| 8,353,920 B2 | 1/2013 | Mikkaichi | 606/145 |
| 8,585,584 B2 * | 11/2013 | Ratnakar | 600/113 |
| 8,602,971 B2 * | 12/2013 | Farr | 600/109 |
| 2002/0007110 A1 * | 1/2002 | Irion | 600/170 |
| 2002/0077593 A1 * | 6/2002 | Perkins et al. | 604/96.01 |
| 2004/0215061 A1 * | 10/2004 | Kimmel et al. | 600/179 |
| 2005/0038317 A1 * | 2/2005 | Ratnakar | 600/101 |
| 2005/0096502 A1 | 5/2005 | Khalili | 600/106 |
| 2005/0182297 A1 * | 8/2005 | Gravenstein et al. | 600/139 |
| 2005/0272977 A1 * | 12/2005 | Saadat et al. | 600/114 |
| 2006/0069302 A1 | 3/2006 | Halvorsen et al. | |
| 2006/0106280 A1 | 5/2006 | Surti et al. | |
| 2006/0149129 A1 * | 7/2006 | Watts et al. | 600/113 |
| 2006/0189845 A1 * | 8/2006 | Maahs et al. | 600/146 |
| 2006/0252993 A1 * | 11/2006 | Freed et al. | 600/146 |
| 2006/0252994 A1 * | 11/2006 | Ratnakar | 600/173 |
| 2007/0049794 A1 * | 3/2007 | Glassenberg et al. | 600/109 |
| 2007/0106113 A1 * | 5/2007 | Ravo | 600/113 |
| 2007/0142702 A1 | 6/2007 | Haller et al. | |
| 2007/0142710 A1 * | 6/2007 | Yokoi et al. | 600/173 |
| 2007/0156021 A1 * | 7/2007 | Morse et al. | 600/167 |
| 2007/0161855 A1 * | 7/2007 | Mikkaichi et al. | 600/113 |
| 2007/0177010 A1 * | 8/2007 | Murata | 348/74 |
| 2007/0185503 A1 * | 8/2007 | Mikkaichi | 606/139 |
| 2007/0197873 A1 | 8/2007 | Birnkrant | |
| 2007/0208252 A1 * | 9/2007 | Makower | 600/424 |
| 2007/0239056 A1 | 10/2007 | Moore | |
| 2007/0255100 A1 * | 11/2007 | Barlow et al. | 600/114 |
| 2007/0276183 A1 * | 11/2007 | Melder | 600/112 |
| 2008/0015413 A1 * | 1/2008 | Barlow et al. | 600/114 |
| 2008/0027279 A1 * | 1/2008 | Abou El Kheir | 600/111 |
| 2008/0051629 A1 * | 2/2008 | Sugiyama et al. | 600/114 |
| 2008/0051655 A1 * | 2/2008 | Sato et al. | 600/439 |
| 2008/0055400 A1 | 3/2008 | Schechterman et al. | |
| 2008/0065104 A1 * | 3/2008 | Larkin et al. | 606/130 |
| 2008/0091064 A1 | 4/2008 | Laser | |
| 2008/0208002 A1 * | 8/2008 | Maruyama | 600/131 |
| 2008/0214890 A1 * | 9/2008 | Motai et al. | 600/107 |
| 2008/0249360 A1 | 10/2008 | Li et al. | |
| 2008/0275298 A1 * | 11/2008 | Ratnakar | 600/109 |
| 2009/0023998 A1 * | 1/2009 | Ratnakar | 600/121 |
| 2009/0030274 A1 * | 1/2009 | Goldfarb et al. | 600/106 |
| 2009/0076329 A1 * | 3/2009 | Su et al. | 600/134 |
| 2009/0125039 A1 * | 5/2009 | Mikkaichi et al. | 606/144 |
| 2009/0143645 A1 * | 6/2009 | Matthes | 600/120 |
| 2009/0240108 A1 | 9/2009 | Shimizu et al. | |
| 2009/0260625 A1 * | 10/2009 | Wondka | 128/203.12 |
| 2009/0318757 A1 * | 12/2009 | Singh | 600/109 |
| 2009/0318798 A1 * | 12/2009 | Singh et al. | 600/424 |
| 2010/0010302 A1 * | 1/2010 | Hadani | 600/109 |
| 2010/0056863 A1 * | 3/2010 | Dejima et al. | 600/106 |
| 2010/0125165 A1 * | 5/2010 | Torii et al. | 600/106 |
| 2010/0174138 A1 * | 7/2010 | Chang et al. | 600/104 |
| 2010/0217076 A1 * | 8/2010 | Ratnakar | 600/104 |
| 2010/0261962 A1 * | 10/2010 | Friedberg | 600/114 |
| 2010/0274188 A1 * | 10/2010 | Chang et al. | 604/96.01 |
| 2011/0160530 A1 * | 6/2011 | Ratnakar | 600/104 |
| 2012/0046669 A1 * | 2/2012 | Duval et al. | 606/130 |

FOREIGN PATENT DOCUMENTS

| | | |
|---|---|---|
| CN | 2706123 | 6/2005 |
| JP | 51046994 B4 | 12/1976 |
| JP | 2005270468 A | 10/2005 |
| WO | 9315648 A1 | 8/1993 |
| WO | 2007137059 A3 | 11/2007 |

* cited by examiner

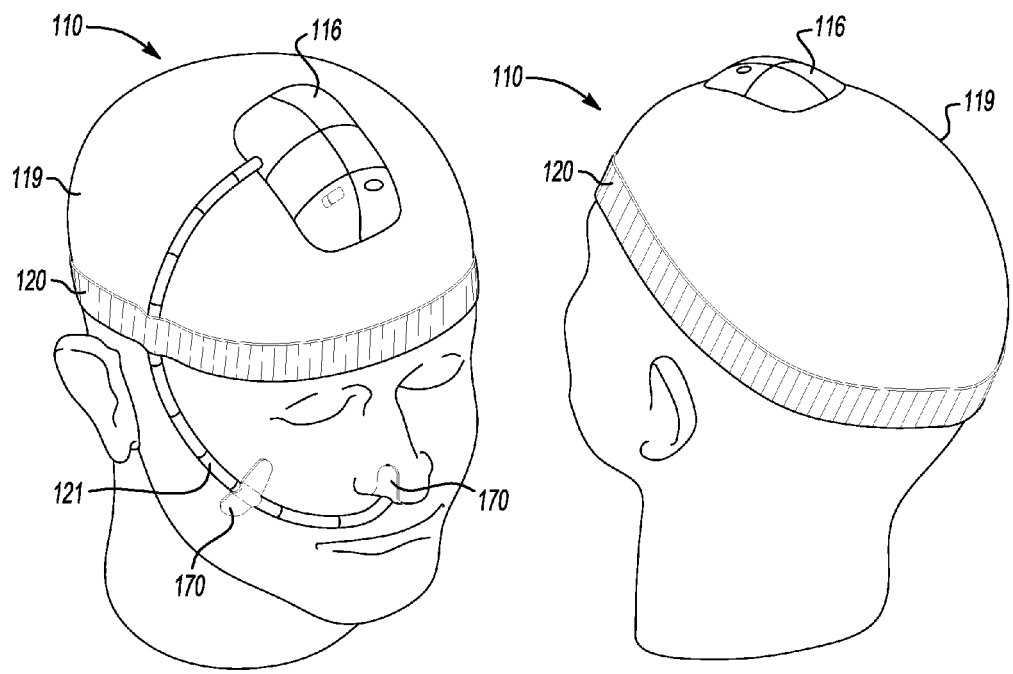
Fig-9A  Fig-9B
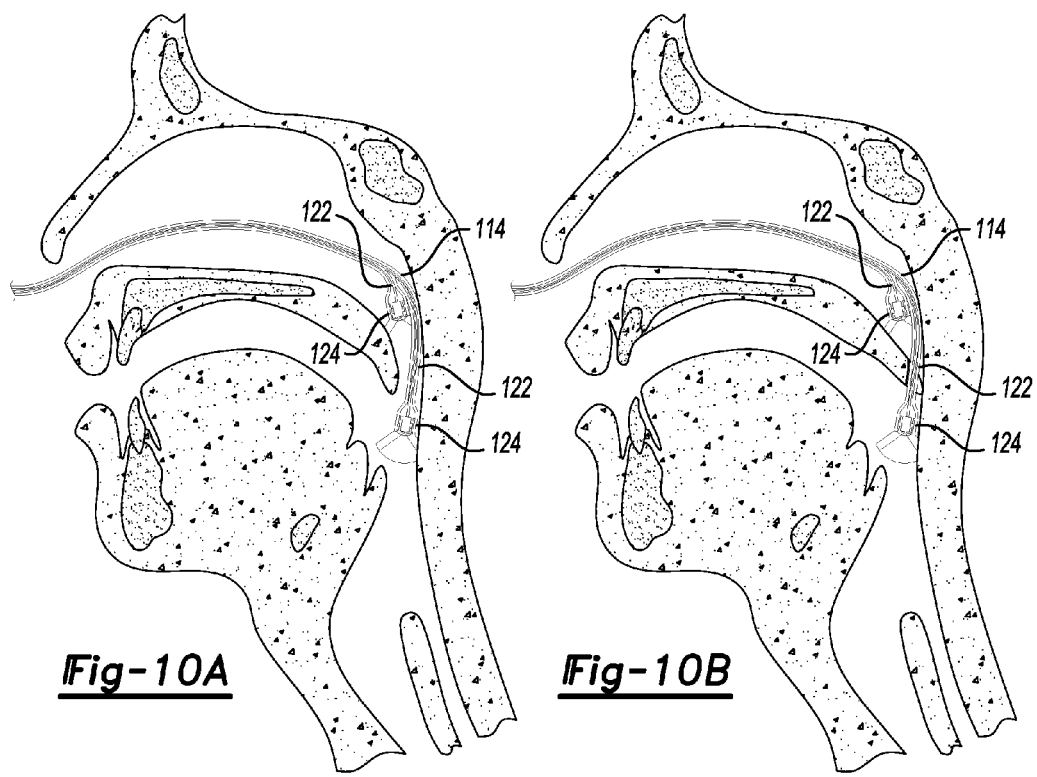
Fig-10A  Fig-10B

ENDOSCOPIC DEVICE AND SYSTEM

CROSS-REFERENCE TO RELATED APPLICATION

This application claims the benefit of U.S. Provisional Application No. 61/321,911, filed Apr. 8, 2010, the contents of which are hereby incorporated by reference in their entirety.

BACKGROUND

Sleep disordered breathing, including snoring and obstructive sleep apnea, affects tens of millions of adults in the United States. It is associated with substantial cardiovascular morbidity and mortality, endocrine disturbances, excessive daytime sleepiness, quality of life and performance deficits, and motor vehicle crashes.

Treatment options include behavioral measures such as weight loss, positive airway pressure therapy, surgery, and oral appliances. All treatments have strengths and weaknesses, and in particular surgical treatment has outcomes that vary widely among patients and procedures.

The evaluation of patients with sleep disordered breathing may improve outcomes of surgical treatment. The goals of such evaluation include characterizing (1) the pattern of airway obstruction (involving primarily the palate/tonsils region, tongue base, epiglottis, and/or lateral pharyngeal walls) and (2) the site of sound production. Existing upper airway examination techniques, however, may not provide an accurate evaluation of the pharynx during natural sleep as explained below.

A flexible endoscope such as the Olympus fiberscope or the Olympus video scope may be utilized to examine a patient's upper airway during wakefulness, natural sleep or sedation. Examination during natural sleep may provide the best results, but attempts to perform traditional natural sleep endoscopy have been largely abandoned for multiple reasons, including the fact that it requires that an operator be present to hold the endoscope in place during the often prolonged period needed for patients to fall asleep with the endoscope in place. The behavior of the upper airway during wakefulness differs dramatically compared to natural sleep, which makes examinations during wakefulness insufficient. Sedation is costly because it requires a controlled environment and the involvement of highly trained personnel and specialized equipment. In addition, sedation may alter the pattern of upper airway obstruction.

Current examinations during wakefulness, sedation, and natural sleep are also limited because their duration is typically no more than 10-15 minutes due to personnel and financial constraints. It is unclear whether this abbreviated examination adequately describes pharyngeal behavior through an entire night of sleep.

There is enthusiasm among clinicians and patients alike for improved surgical evaluation techniques, particularly techniques that provide an accurate, dynamic assessment of the upper airway during natural sleep without the need for sedation, the presence of a clinician, or the associated costs.

SUMMARY

An endoscopic device may include a catheter or tubing and at least two optical sensors spaced apart from each other along the catheter or tubing such that, for example, image information from different regions of a body lumen partially or completely separated by an obstruction is captured when each of the at least two optical sensors is disposed within one of the regions and activated.

BRIEF DESCRIPTION OF THE DRAWINGS

FIGS. 9A and 9B are front and rear schematic views, respectively, of the endoscopic system of FIG. 2 fitted to a patient's head in the in-use position.
FIGS. 10A and 10B are side views, in sagittal cross-section, of the patient's head and optical sensor arrangement of FIGS. 9A and 9B.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
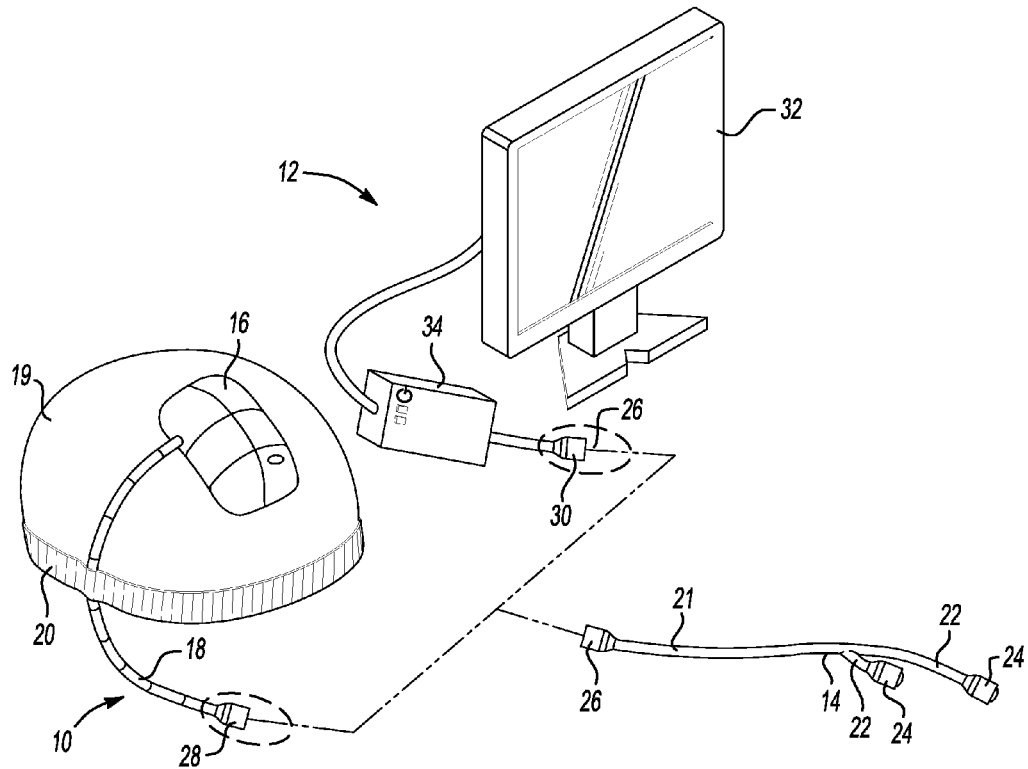
FIG. 1 is a schematic diagram of an endoscopic system.

Referring to FIG. 1, an embodiment of an endoscopic system 10 may be used to collect visual and/or audio information from a patient's airway. This information may be displayed and/or played by the output system 12. The endoscopic system 10 may include an optical sensor arrangement 14, a data and/or power module 16, a sensor cord 18 connecting the sensor arrangement 14 and module 16, and a skullcap 19. Other arrangements are also possible and will be discussed in further detail below.

The module 16 may be removably attached with the skullcap 19 via VELCRO, a snap feature or other suitable attachment mechanism. The skullcap 19 may include an elastic band 20 configured to secure the skullcap 19 and sensor cord 18 to a patient's head.

The sensor arrangement 14, in the embodiment of FIG. 1, includes a body portion 21 and a pair of legs 22 of differing lengths projecting there from. Each of the legs 22 has an optical sensor 24 disposed at an end thereof. The sensor arrangement 14 also includes a connector 26 (e.g., a USB port, a fiber optic connector, etc.) disposed at an end of the body portion 21 opposite the legs 22 and capable of, for example, connecting the optical sensors 24 with a mating connector 28 of the sensor cord 18 and/or a mating connector 30 of the display system 12.

When the sensor arrangement 14 is connected with the module 16, the module 16 may store information received from the sensor arrangement 14 for later access. For example, the module 16 may store collected information while a patient is asleep. An investigator may then access the stored information at a later time. When the sensor arrangement 14 is connected with the display system 12, information captured by the sensor arrangement 14 may be viewed in real-time.

The display system 12 may include a display screen 32 and any suitable/known decoder device 34 (e.g., a non-wearable version of module 16, a video monitor, a smart phone, a personal computer with suitable hardware/software, etc.) The decoder device 34 may be configured to interpret information from the sensor arrangement 14 and generate appropriate signals for (i) display and/or play by the display screen 32 and/or (ii) data storage in a storage device (not shown).

Figure 2:
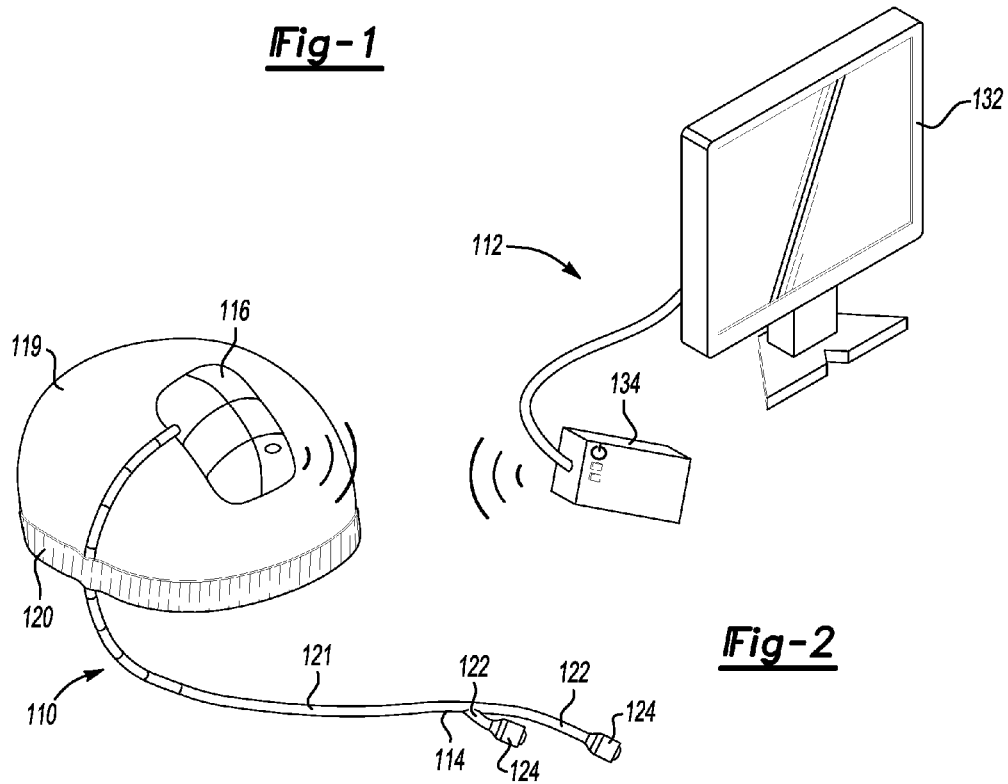
FIG. 2 is a schematic diagram of another endoscopic system.

Referring to FIG. 2, the sensor arrangement 114 is directly connected with the module 116. The module 116 may wirelessly transmit (and/or store) information from the sensor arrangement 114 to the decoder device 134 for real-time display and/or play. Other arrangements are, of course, also possible. For example, the module 116 may wirelessly transmit information from the sensor arrangement 114 to a remote storage device (not shown). Alternatively, the module 116 may store the information from the sensor arrangement 114 for later access, etc.

Figure 3:
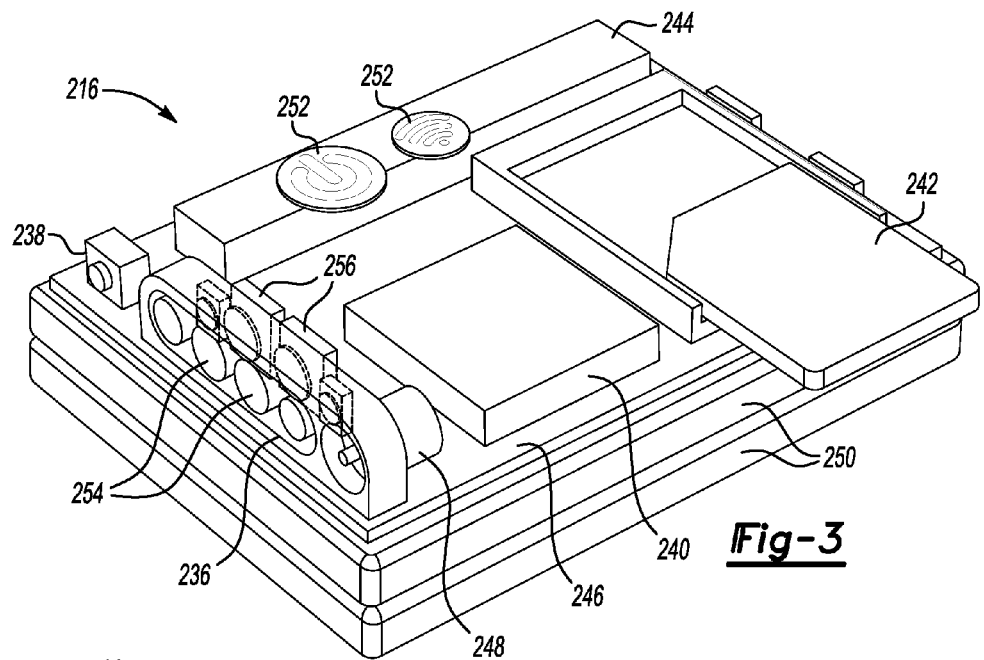
FIG. 3 is a schematic diagram of a data and/or power module of an endoscopic system.

Referring to FIG. 3, an embodiment of a data and/or power module 216 may include a bundle coupling 236, a microphone input 238, a microprocessor 240, a memory 242 (e.g., a card reader, etc.), and a radiofrequency transmitter 244 all mounted on a printed circuit board 246. The module 216 may also include a rechargeable power source 250 (e.g., rechargeable batteries) disposed, in this embodiment, on a side of the circuit board 246 opposite the microprocessor 240, and various switches 252 (e.g., a power switch, a microphone switch, etc.) The coupling 236 may include a recharging port 248, image sensors 254, and associated LEDs 256. Hence, the module 216 is self-contained and may operate untethered. That is, it may operate without being attached via cording to a separate power source, processor, memory, etc. (unlike certain conventional arrangements).

In other embodiments, the image sensors 254, for example, may be replaced with suitable connectors for cameras; the transmitter 244 may be replaced with a suitable wired data output, etc.

Information received via the coupling 236 and/or the microphone input 238 may be processed by the microprocessor 240 in any suitable/known fashion and stored in the memory 242 and/or wirelessly transmitted via the radiofrequency transmitter 244.

Figure 4:
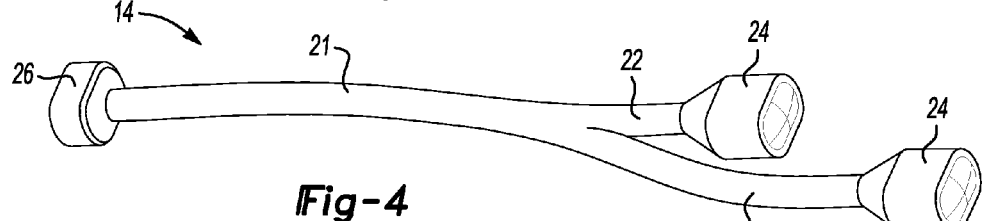
FIG. 4 is a schematic diagram of the sensor arrangement of the endoscopic system of FIG. 1.

Referring to FIG. 4, the sensor arrangement 14 of FIG. 1 is shown in further detail. The legs 22 are of different lengths such that the optical sensor 24 disposed at the end of the longer leg 22 may capture images from an area of a patient's airway different than the images captured by the optical sensor 24 disposed at the end of the shorter leg 22. Given this arrangement, different regions within the airway may be observed at the same time, even if there is an intervening structure that obstructs the simultaneous visualization of both (or all) areas with a single optical sensor. For snoring and sleep apnea, as an example, the soft palate can isolate two areas of the airway (above and below) if it completely or partially obstructs the airway. The use of two cameras or other methods of image acquisition from two sites (as opposed to one) enables the simultaneous visualization of the two areas.

In the embodiment of FIG. 4, the optical sensors 24 are spaced apart at a distance that may be greater than or equal to 5 mm. That is, the length of the longer leg 22 may be at least 5 mm greater than that of the shorter leg 22. In other embodiments, the optical sensors 24 may be spaced at any distance suitable for capturing images of different regions of a patient's airway (e.g., 5 mm, 10 mm, 50 mm, etc.)

Some embodiments may have more or less than two legs 22 and two associated optical sensors 24. For example, a sensor arrangement may have three legs each with an optical sensor disposed at an end thereof. The number of legs (and thus the number of optical sensors) may, however, be limited by the effective diameter of a patient's airway.

Figure 5:
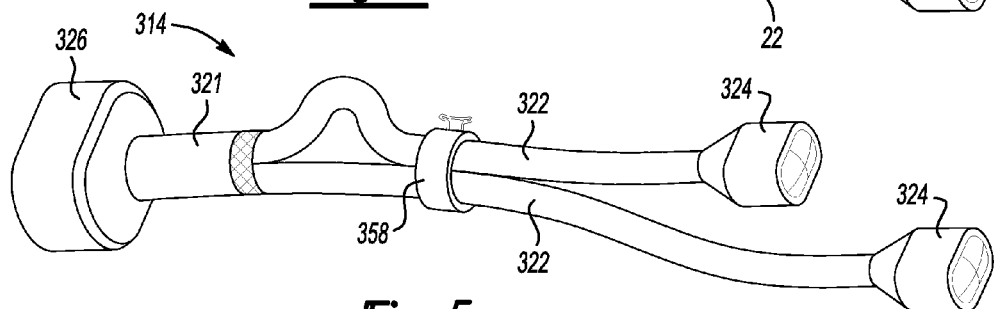
FIG. 5 is a schematic diagram of another sensor arrangement for an endoscopic system.

Referring to FIG. 5, the legs 322 of the sensor arrangement 314 have the same or different lengths, but a clamp 358 (band, locking mechanism, etc.) may be used to effectively change the length of one of the legs 322 relative to the other. This arrangement may be used to tailor the distance between the optical sensors 324 for a particular patient while using a standard sensor arrangement.

Figure 6:
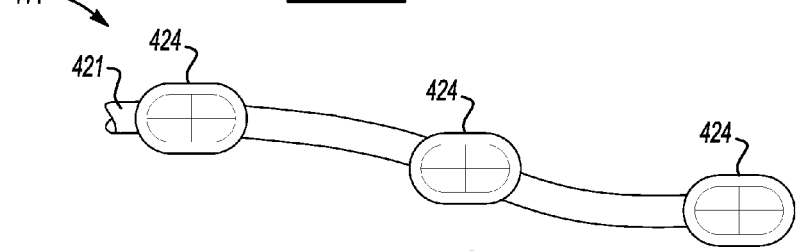
FIG. 6 is a schematic diagram of yet another sensor arrangement for an endoscopic system.

Referring to FIG. 6, the optical sensors 424 are disposed (and spaced apart) along the body portion 421 of the sensor arrangement 414. This arrangement, relative to the embodiments of FIGS. 4 and 5, may allow the packaging of several of the optical sensors 424 without substantially altering the diameter of the sensor arrangement 414.

Figure 7A:
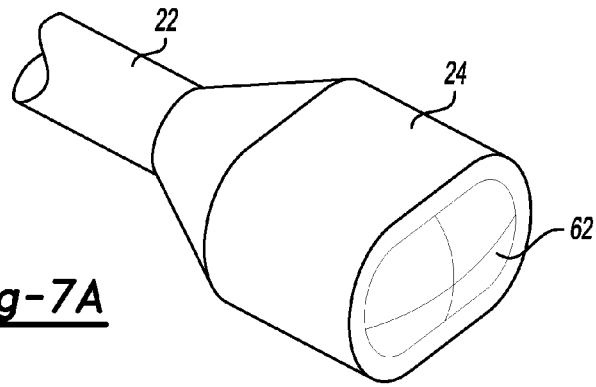
FIG. 7A is a perspective view of one of the optical sensors of the endoscopic system of FIG. 1.
Figure 7B:
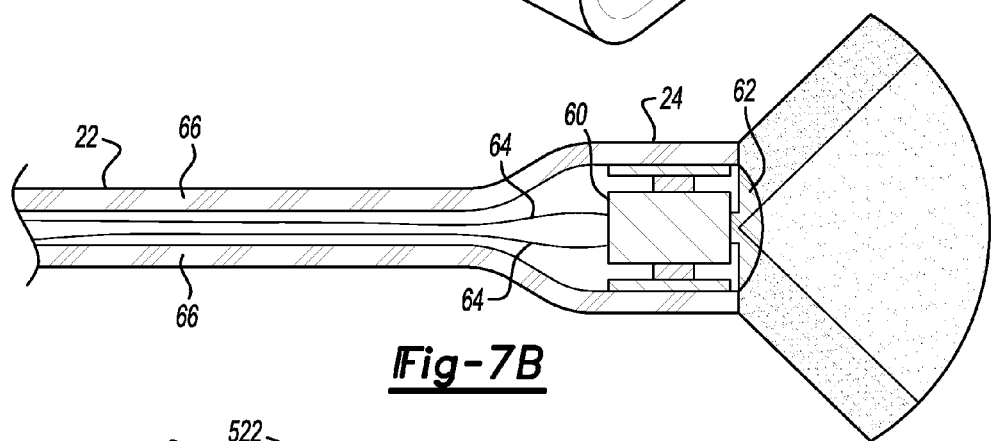
FIG. 7B is a side view, in cross-section, of the optical sensor of FIG. 7A.

Referring to FIGS. 7A and 7B, one of the optical sensors 24 of FIG. 1 is shown in further detail. In this embodiment, the optical sensor 24 includes a camera 60 and associated lens 62. The camera 60 may receive power from and transmit image information to the module 16 of FIG. 1 via electrical/communication lines 64. Illumination fibers 66 in optical communication with, for example, LEDs within the module 16 of FIG. 1 are disposed within the leg 22. The illumination fibers 66 provide light for the camera 60.

The optical sensor 24 may have a diameter ranging from approximately 6 mm to 10 mm. The leg 22 may have a diameter ranging from approximately 2 mm to 5 mm. Other diameters and sizes, however, are also possible depending on, for example, camera size, fiber diameter, etc.

Figure 8A:
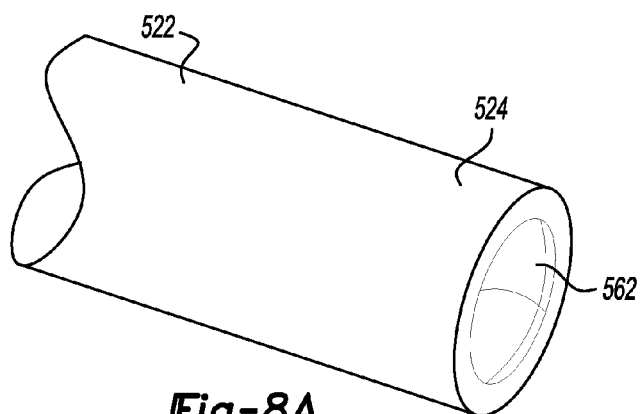
FIG. 8A is a perspective view of another optical sensor of an endoscopic system.
Figure 8B:
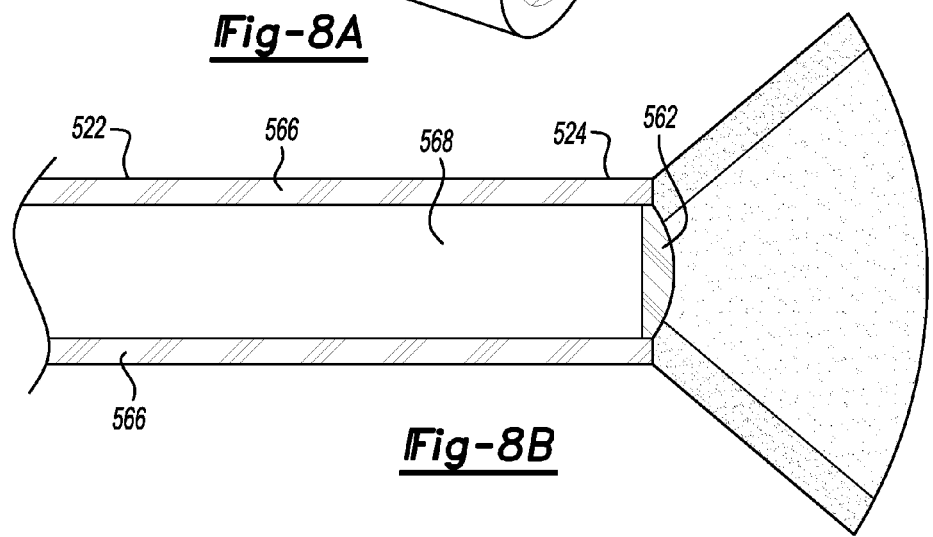
FIG. 8B is a side view, in cross-section, of the optical sensor of FIG. 8A.

Referring to FIGS. 8A and 8B, another embodiment of an optical sensor 524 is shown in further detail. The optical sensor 524 includes a video fiber optic element 568 and associated lens 562. Because the optical sensor 524 does not include an internal camera (similar to the optical sensor 24 of FIGS. 7A and 7B), its diameter may range in size from approximately 3 mm to 8 mm. Other diameters and sizes, however, are also possible depending on, for example, fiber diameter, etc. In other embodiments, any suitable/known optical sensor may be used.

Referring to FIGS. 9A, 9B, 10A and 10B, the endoscopic system 110 of FIG. 2 is fitted to a patient's head. The sensor arrangement 114 is positioned such that the optical sensors 124 capture image information from different regions within the patient's airway. More specifically, the legs 122 are arranged and the optical sensors 124 are positioned, in this example, such that the optical sensors 124 capture image information from the retropalatal and retrolingual regions of the patient's pharynx regardless of whether there is an obstruction between the two regions (e.g., the soft palate obstructing the airway, as in FIG. 10B). The sensor arrangement 114 may also be arranged, of course, to capture, for example, image information from a single region or multiple overlapping or non-overlapping regions of any body lumen.

The skullcap 119 is placed over the patient's head and the module 116 is attached thereto with, for example, a snap feature (not shown). The body portion 121 is attached to the patient's cheek and nose with adhesive 170. This arrangement may permit the patient to wear (attended or unattended) the endoscopic system 110 for extended periods of time while image information from their airway is collected and, for example, stored within the module 116.

Figure 11A:
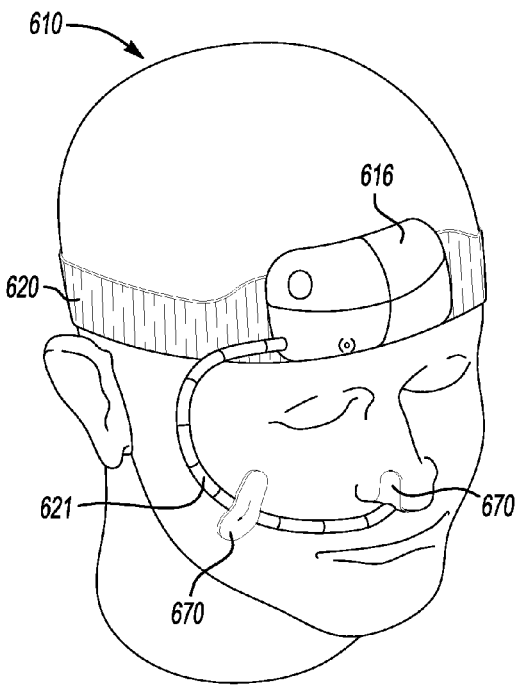
FIGS. 11A and 11B are front and rear schematic views, respectively, of another embodiment of an endoscopic system fitted to a patient's head in the in-use position.
Figure 11B:
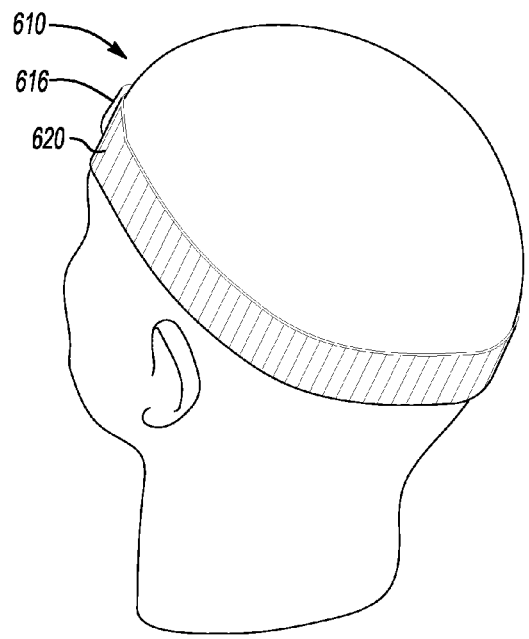

Referring to FIGS. 11A and 11B, another embodiment of an endoscopic system 610 is fitted to a patient's head. In this embodiment, the headband 620 is larger than in the embodiments of, for example, FIGS. 1 and 2. Hence, the module 616 may be attached directly to the front of the headband 620 (or the rear/side as desired).

Figure 12A:
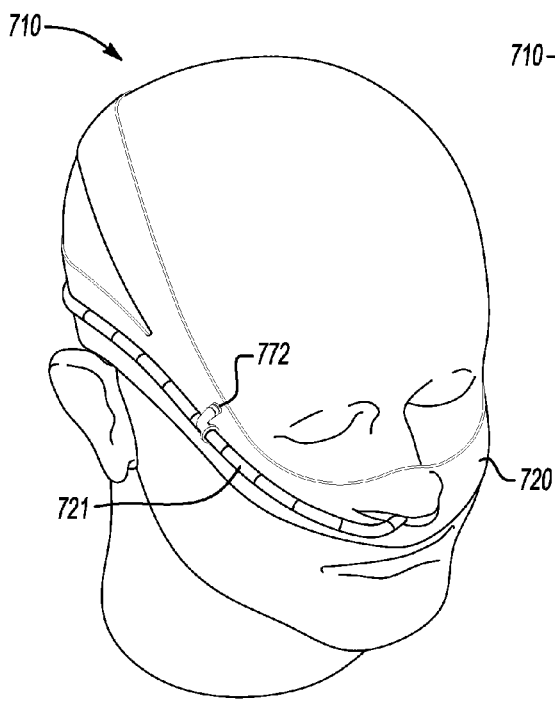
FIGS. 12A and 12B are front and rear schematic views, respectively, of yet another endoscopic system fitted to a patient's head in the in-use position.
Figure 12B:
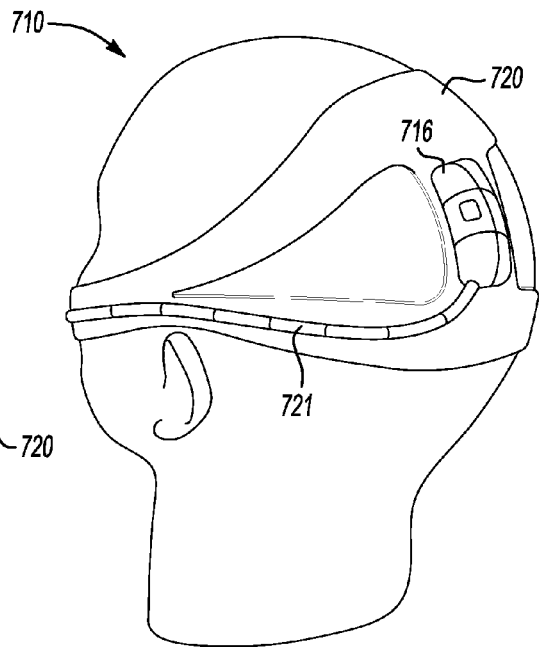

Referring to FIGS. 12A and 12B, yet another embodiment of an endoscopic system 710 is fitted to a patient's head. The headband 720, in this embodiment, encompasses the nose of the patient and provides a harness in the rear where the module 716 may be attached. In this embodiment, the body portion 721 need not be attached directly to the patient's face. Rather, the body portion 721 is attached to the headband 720 via snaps 772 or other suitable attachment features. Other arrangements are also possible.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention. As an example, certain embodiments may be used to collect images over a period of time from any body lumen (e.g., nasal cavity, esophagus, stomach, small intestine and large intestine, etc.) As another example, while endoscopic systems including either an internal (to the body) camera with an external light source and battery or an external camera, light source and battery have been explicitly disclosed, other embodiments of endoscopic systems may include an internal camera, battery and light source, an internal camera and light source with an external battery, an internal camera and battery with an external light source, or any other internal/external combination of components. As yet another example, certain embodiments may be fitted to any part of a patient's body via suitable cuffs/adhesives/bands/pockets/etc.

What is claimed is:

1. An endoscopic device comprising:
    a catheter or tubing having at least two branches of unequal length and substantially same diameter extending from and fixed relative to a common joint; and
    at least two optical sensors disposed on the branches and oriented in a same general direction such that the sensors are positioned at least 5 mm apart from each other on the branches to capture image information from different regions of a body lumen from the same general direction when disposed within the body lumen and activated.

2. The device of claim 1 wherein the at least two optical sensors are positioned at least 10 mm apart from each other on the branches.

3. The device of claim 1 further comprising an adjustment mechanism configured to alter at least one of an effective length of at least one of the branches and a distance between the image sensors.

4. An endoscopic device comprising:
    a catheter or tubing having at least two branches of unequal length extending from and fixed relative to a common joint; and
    at least two optical sensors disposed on the branches and oriented in a same general direction such that the sensors are positioned apart from each other on the branches such that image information from different regions of a body lumen partially or completely separated by an obstruction is captured when each of the at least two optical sensors is disposed within one of the regions and activated.

5. The device of claim 4 wherein the at least two optical sensors are positioned at least 5 mm apart from each other on the branches.

6. The device of claim 4 wherein the at least two optical sensors are positioned at least 10 mm apart from each other on the branches.

7. The device of claim 4 further comprising an adjustment mechanism configured to alter at least one of an effective length of at least one of the branches and a distance between the image sensors.

8. An endoscopic device comprising:
    a catheter or tubing having at least two branches of unequal length extending from and fixed relative to a common joint; and
    at least two optical sensors disposed on the branches, oriented in a same general direction and positioned away from each other on the branches such that image information from each of a retropalatal region and retrolingual region of a patient's upper airway is captured when (i) one of the at least two optical sensors is disposed within the retropalatal region and another of the at least two optical sensors is disposed within the retrolingual region, and the retropalatal and retrolingual regions are at least partially separated by an obstruction and (ii) the at least two optical sensors are activated.

9. The device of claim 8 wherein the at least two optical sensors are positioned at least 5 mm apart from each other on the branches.

10. The device of claim 8 wherein the at least two optical sensors are positioned at least 10 mm apart from each other on the branches.

11. The device of claim 8 further comprising an adjustment mechanism configured to alter at least one of an effective length of at least one of the branches and a distance between the image sensors.

* * * * *